United States Patent [19]

Furihata

[11] 4,414,608

[45] Nov. 8, 1983

[54] ENDOSCOPE WITH ADAPTER

[75] Inventor: Hiroyuki Furihata, Hamura, Japan

[73] Assignee: Olympus Optical Co., Ltd., Tokyo, Japan

[21] Appl. No.: 288,404

[22] Filed: Jul. 30, 1981

[30] Foreign Application Priority Data

Aug. 7, 1980 [JP] Japan .................. 55-107779

[51] Int. Cl.³ .............................. F21V 7/04
[52] U.S. Cl. .................... 362/32; 362/226;
362/804; 128/4; 128/6; 352/198; 352/200;
352/203; 354/62; 354/126; 354/132
[58] Field of Search ............ 362/32, 804, 226;
128/4, 6; 354/62, 126, 132; 352/198, 200, 203

[56] References Cited

U.S. PATENT DOCUMENTS 3,638,013  1/1972  Keller .
3,730,645  5/1973  Mashakaru et al. .
4,053,756  10/1977  Takahashi .................... 362/32 X
4,110,820  8/1978  Konoshima .................. 362/32 X
4,330,274  5/1982  Friedman et al. ........... 362/804 X
4,356,534  10/1982  Hattori ......................... 362/32
4,366,529  12/1982  Takahashi et al. ........... 362/32 X

FOREIGN PATENT DOCUMENTS 52-25036  6/1977  Japan .
55-87503  6/1980  Japan .

Primary Examiner—Stephen J. Lechert, Jr.
Attorney, Agent, or Firm—Frishauf, Holtz, Goodman and Woodward

[57] ABSTRACT

An endoscope with an adapter used in combination with a light source unit including a socket having an electrical contact and a light source for illumination. The adapter includes a main body portion having a first connecting portion capable of being removably fitted with a connector of an endoscope and a second connecting portion capable of being removably attached to the socket, first electrical contacts disposed at the first connecting portion to be electrically connected with electrical contacts of the connector, second electrical contacts disposed at the second connecting portion connected to the first electrical contacts so as to be electrically connected with the electrical contact of the socket and a bore optically connecting a light guide in a projected pipe of the endoscope with the illuminating light source of the light source unit.

11 Claims, 5 Drawing Figures

ENDOSCOPE WITH ADAPTER

BACKGROUND OF THE INVENTION

This invention relates to an endoscope with an adapter adapted to be optically, electrically connected with the socket of a light source-power source unit.

In many currently used endoscopes, the connector is designed in conformity to the socket of a common light source-power source unit so that these endoscopes may suitably be applied to such common light source-power source units.

With the remarkable progress of the endoscope in recent years, however, there have been aroused a demand for a drastic change of the form of the connector in response to several circumstances including proposals for e.g. conversion of the connector section into an airtight construction which ensures disinfection of the whole endoscope body with a medical fluid or conversion of the endoscope body into a floating type without grounding. If the form of the connector is changed in this way, however, the connector will fail to suit the form or type of the conventionally used light source unit. In this case, it has been a common idea to produce and use a light source unit which can conform to a new-type endoscope.

Since the light source unit is very expensive and considerably durable, it is uneconomical and rather impractical to change the light source unit with every development of a new-type endoscope.

SUMMARY OF THE INVENTION

The object of this invention is to provide an endoscope with an adapter capable of affording itself new functions by designing the connector of the endoscope so as to be able to be connected with the socket of a light source unit not directly but by means of an adapter.

DETAILED DESCRIPTION OF THE PREFERRED EMBODIMENTS

Figure 1:
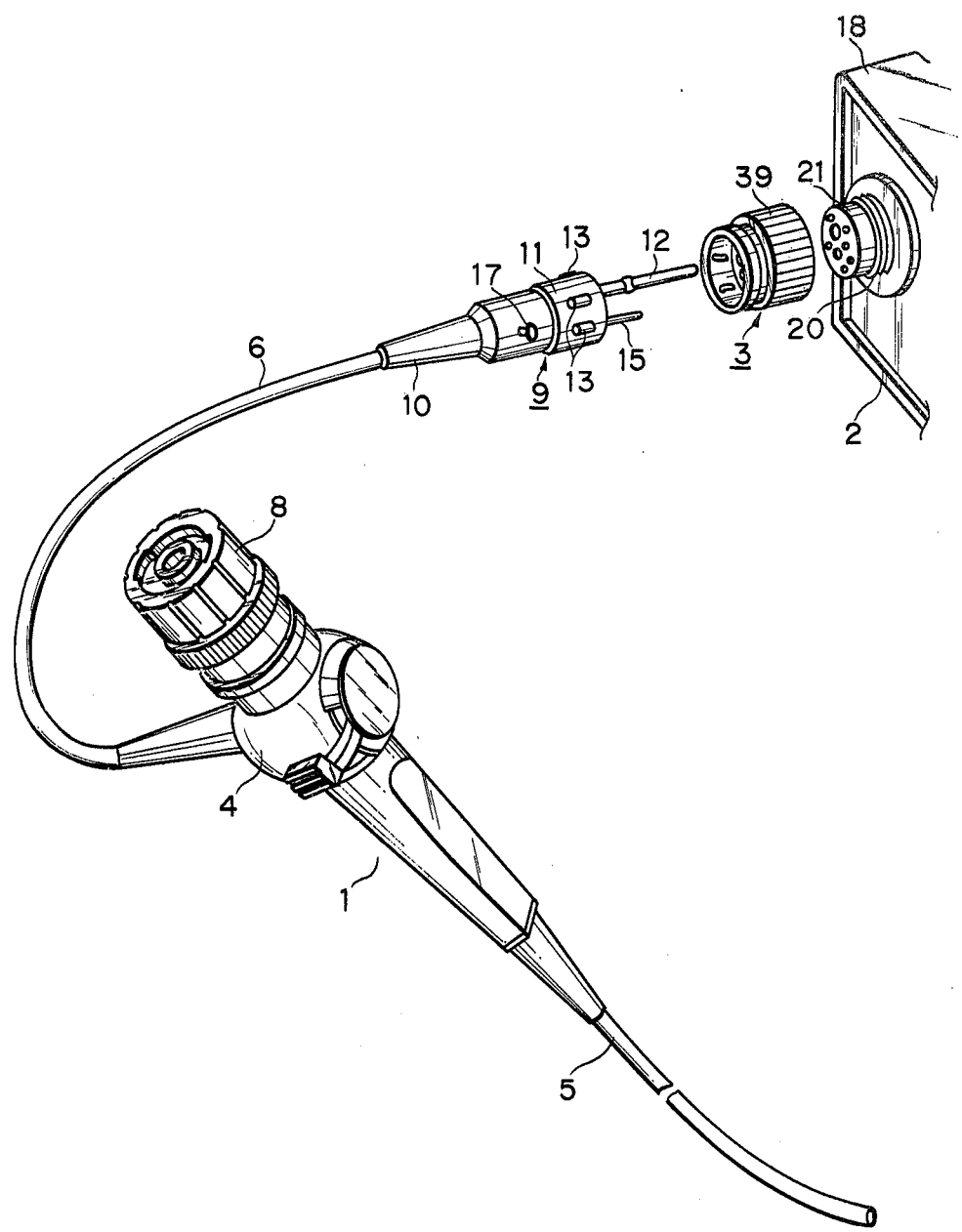
FIG. 1 is a perspective view of an endoscope with an adapter according to an embodiment of this invention.
Figure 2:
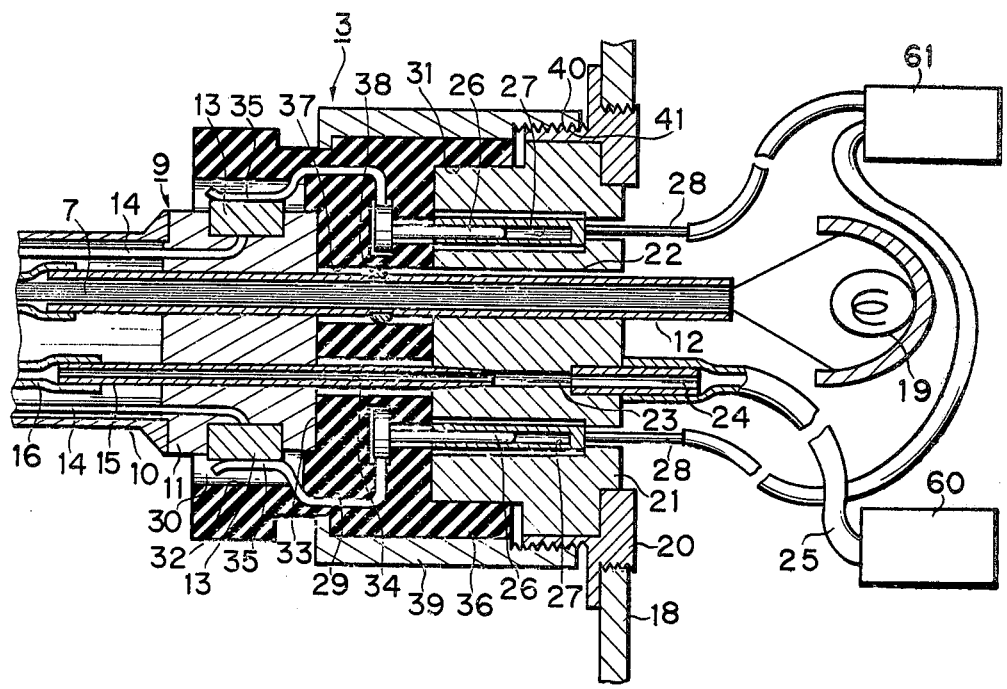
FIG. 2 is a sectional view of the endoscope with an adapter connected with a conventional light source-power source unit.
Figure 3:
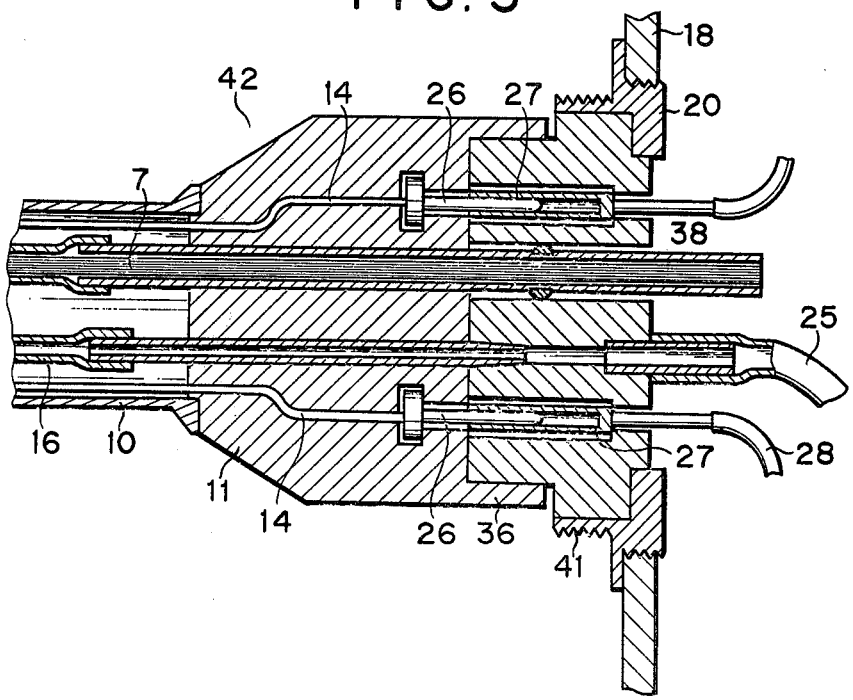
FIG. 3 is a sectional view showing a modification of the endoscope connected with the light source-power source unit of FIG. 2.

Referring now to FIGS. 1 to 3, there will be described an endoscope with an adapter according to an embodiment of this invention.

In FIG. 1, there are shown an endoscope 1 of a new style and a conventional-type light source unit 2 which are to be optically, electrically and mechanically connected with each other by means of an adapter 3. The endoscope 1 includes a control section 4, a flexible insert section 5 coupled therewith, and a flexible light guide cable 6 also coupled with the control section 4. As shown in FIG. 2, a light guide 7 formed of an optical fiber bundle is passed through the light guide cable 6. The light guide 7 extends through the control section 4 and the insert section 5 to reach the distal end of the insert section 5, through which illumination light is transmitted and emitted from an illumination window (not shown). Also, an image guide (not shown) is passed through the control section 4 and the insert section 5, connecting an observation window (not shown) at the distal end of the insert section 5 with an eyepiece section 8 at the control section 4.

A connector 9 is attached to the extended end of the light cable 6. The connector 9 is composed of a cylindrical connector body 10 and a cylindrical plug member 11 coaxially fixed to the distal end of the connector body 10. The plug member 11 is formed of electrically insulating material such as plastics. A projected pipe 12 having the light guide 7 built-in is penetratingly fixed to the plug member 11, protruding in a straight line from the distal end face of the plug member 11. A plurality of electrical contacts 13, projected and exposed, are fixed at regular circumferential intervals on the outer circumferential side face of the plug member 11. These electrical contacts 13 are severally connected with the extended ends of conductors 14 which pass through the light guide cable 6 to extend into the plug member 11. These conductors 14 serve as, for example, signal lines for photographing and power supply lines for motor drive. Further, the plug member 11 is fixedly fitted with an air-feed pipe 15 which passes through the plug member 11 in parallel with the projected pipe 12. The air-feed pipe 15 is connected at its proximal end with an air tube 16 which passes through the light guide cable 6. The distal end of the air-feed pipe 15 protrudes from the distal end face of the plug member 11, leaving a shorter projection than the projected pipe 12 does. An air-feed mouthpiece 17 is disposed on the counter circumferential side face of the connector body 10.

The light source unit 2 is composed of a casing 18, an illumination lamp 19, and a cylindrical socket 21 attached by means of a fixing ring 20 to the outer surface of a side wall of the casing 18 which faces the illumination lamp 19 in the light emitting direction of the lamp 19. The socket 21, which is formed of electrically insulating material such as plastics, is provided with a hole 22 through which the projected pipe 12 is passed and an air hole 23 in which the distal end portion of the air-feed pipe 15 is fitted airtightly, both these holes extending in parallel with the central axis of the socket 21. An air tube 25 is connected with the distal end portion of the air hole 23 by means of a connecting pipe 24. Thus, the air hole 23 is connected with an air pump 60 in the light source unit 2 by means of the air tube 25. Moreover, the socket 21 is provided with receptors 27 as electrical contacts in and with which contact pins 26 of the adapter 3 mentioned later are fitted and connected. These receptors 27 are severally connected with conductors 28 on the side of the light source unit 2, the conductors 28 being severally connected with electric devices inside the light source unit 2, such as an electric eye (EE) control circuit, a power source 61, etc.

The adapter 3, which has its cylindrical main body portion 29 formed of electrically insulating material such as plastics, is provided at one end side with a first connecting portion 30 for removably connecting the connector 9, and at the other end side with a second connecting portion 31 for removably connecting the socket 21. As shown in FIG. 2, the first connecting portion 30 includes a circular cavity portion 32 formed in one end face of the main body portion 29 so as to receive the plug member 11 of the connector 9, and a circular recess 33 at the bottom of the cavity portion 32 having its inside diameter set so that the distal end portion of the plug member 11 may be fitted tight in the recess 33. In the vicinity of the inner circumferential surface of the cavity portion 32, moreover, there are arranged electrical contact strips 35 formed of a plurality of leaf springs constituting first electrical contacts. These contact strips 35 correspond to the electrical contacts 13 on the side of the connector 9 and are projected so as to be able to be displaced toward the inner circumferential surface of the cavity portion 32. The contact strips 35 are to be severally pressed against the electrical contacts 13 of the connector 9 to be electrically connected therewith when the connector 9 is inserted in the cavity portion 32.

The second connecting portion 31 includes an annular collar 36 protruding from the other end face of the main body portion 29 and having its inner circumferential surface fitted on the outer circumferential surface of the socket 21, and the aforementioned contact pins 26 as second electrical contacts protruding from the other end face of the main body portion 29 located inside the collar 36. The contact pins 26 are to be fitted in the cylindrical receptors 27 in the bore formed in the socket 21 when the adapter 3 is connected to the socket 21. The contact pins 26 are electrically connected with their corresponding electrical contact strips 35.

Formed in the main body portion 29 of the adapter 3 are a bore 37 through which the projected pipe 12 is passed and a bore 34 through which the air-feed pipe 15 is passed, both these bores extending in parallel with the axis of the adapter 3. Further, an elastic ring 38 is put on the circumferential surface of the projected pipe 12 located inside the bore 37, abutting hard on the inner surface of the bore 37.

A cylindrical fitting ring 39 is put on the outer circumferential surface of the adapter 3 so as to be able to rotate on its central axis and to move through a fixed distance along the central axis. An internal thread 40 is formed in the inner circumferential surface of the distal end portion of the fitting ring 39. The adapter 3 is securely fixed to the socket 21 by screwing the internal thread 40 onto an external thread 41 formed in the outer circumferential surface of the fixing ring 20 so that a projected portion at the proximal end of the fitting ring 39 may press a stepped portion formed on the outer circumferential surface of the main body portion 29 toward the socket 21. Namely, the fitting ring 39 constitutes a fixing means for fixing the adapter 3 to the light source unit 2.

It is not limited to the adapter 3 of the aforementioned construction that can be connected with the socket 21. As shown in FIG. 3, a connector 42 of any type used in a conventional endoscope can be connected directly with the socket 21.

As is evident from FIG. 3, the connector 42 has the same construction as that of the second connecting portion 31 of the adapter 3, so that like portions are designated by like reference numerals without repetition of detailed description thereof. In the construction of FIG. 3, however, the contact pins 26 are connected directly with their corresponding conductors 14.

Now there will be described the use and function of the assembly of the above-mentioned embodiment.

First, when using the endoscope 1 with the new-type connector 9 in combination with the conventional-type light source unit 2, the adapter 3 is fitted on the socket 21, and then the connector 9 is fitted in the adapter 3, as shown in FIG. 2. Thus, by the use of the adapter 3, the endoscope 1 with the new-type connector 9 can be adapted to the conventional-type light source unit 2.

When using the endoscope with the conventional-type connector 42 in combination with the same light source unit 2, on the other hand, the connector 42 can be connected directly with the socket 21 without using the adapter 3, as shown in FIG. 3.

It is to be understood that the new-type connector 9 can be connected without using the adapter 3 if a light source unit adaptable to the connector 9 is provided.

When using such a novel light source unit with the endoscope having the conventional-type connector 42, moreover, the connector 42 can be connected by means of a separately provided adapter. Such adapter is to include a first connecting portion capable of being removably connected with the connector of the endoscope on one end side of the main body portion of the adapter, and a second connecting portion capable of being removably connected to the socket of the light source unit on the other end side of the main body portion, as well as first electrical contacts to be connected with the electrical contacts on the connector side when the connector is connected to the adapter, and second electrical contacts to be connected with the electrical contacts on the socket side when the adapter is connected to the socket so that the first and second electrical contacts are allowed to conduct.

Figure 4:
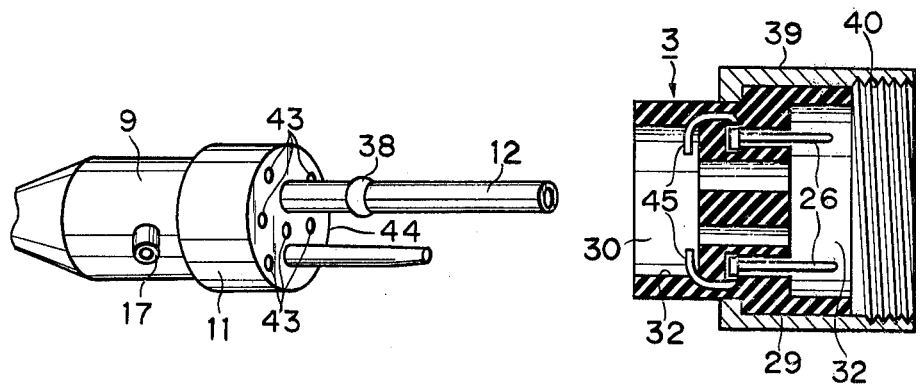
FIG. 4 is a perspective view of an endoscope with an adapter according to another embodiment.

FIG. 4 shows another embodiment of this invention, in which electrical contacts 43 formed in the connector 9 of the endoscope are exposed on a distal end face 44 of the plug member 11, and electrical contact strips 45 constituting first electrical contacts on the side of the adapter 3 corresponding to the electrical contacts 43 protrude from the bottom of the cavity 32 of the main body portion 29.

Figure 5:
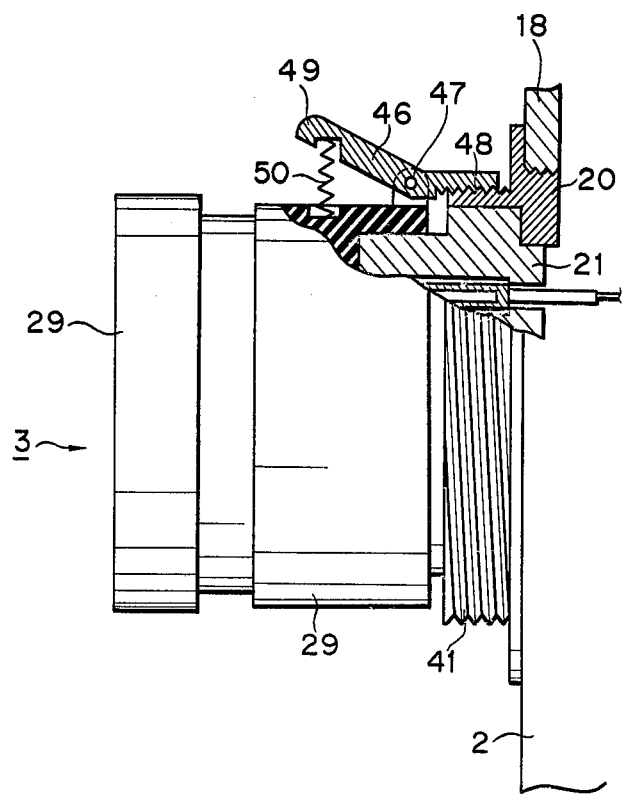
FIG. 5 is a broken away, side view of an endoscope with adapter according to still another embodiment.

FIG. 5 shows still another embodiment of the invention, in which the adapter 3 is engagedly fixed to the fixing ring 20 by means of an engaging lever 46 instead of using the fitting ring 39. In this case, the middle portion of the engaging lever 46 is pivotally mounted on a projection 47 which is formed on the outer circumferential surface of the main body portion 29, and a rugged portion 48 capable of engaging the external thread 41 of the fixing ring 20 is formed on the inner surface of one end portion of the level 46 as an engaging end so that the level 46 may be rocked by pressing the other end of the lever 46 as an operating portion 49 with a finger. A compression spring 50 is interposed between the operating portion 49 and the main body portion 29 so that the engaging lever 46 may be urged to rock in the engaging direction. Thus, the engaging end of the engaging lever 46 may automatically be engaged with the external thread 41 of the fixing ring 20 to attach the adapter 3 fixedly to the socket 21 by releasing the press of a finger on the operating portion 49 after fitting the adapter 3 in the socket 21 with the engaging end of the lever 46 rocked by depressing the operating portion 49 with the finger.

In the use of the adapter according to this invention, the adapter may be attached to and detached from the socket after it is previously fitted with the connector.

According to this invention, as described above, a light source unit may be used directly with endoscopes with connectors of different types by providing an adapter. That is, it is unnecessary to change the light source unit according to the type of the endoscope used. Accordingly, a single light source unit, which is generally expensive, can enjoy prolonged use with endoscopes of various types, resulting in an improvement in economical efficiency. Further, the construction of the connector can be changed variously without regard to the type of the socket of the light source unit used. For example, the connector section may enjoy an airtight or wetproof construction, or the endoscope body may be of a floating type without grounding. The use of a floating-type endoscope can protect the human body against electrical hazards. Further, the use of a wetproof or watertight connector will greatly reduce the incidence of troubles due to leakage of water and the like. It will be possible, for example, to eliminate electrical difficulties attributable to the existence of water.

Thus, according to this invention, the connector can very easily be provided with various improved functions and durability to ensure a high-performance endoscope apparatus.

I claim:

1. An endoscope with an adapter used in combination with a light source unit including a socket having an electrical contact and a light source for illumination, comprising:

an endoscope including a connector having at least one electrical contact and an elongated pipe projecting from said connector and having a light guide therein; and an adapter including a main body portion having: a first connection portion adapted to be removably coupled to said connector of said endoscope and a second connecting portion adapted to be removably attached to said socket of said light source unit; a first electrical contact disposed at said first connecting portion for electrically connecting with said at least one electrical contact of said connector when said connector is attached to said first connecting portion; a second electrical contact disposed at said second connecting portion for electrically connecting with said electrical contact of said socket when said second connecting portion is attached to said socket; and means for electrically connecting said first and second electrical contacts together; said adapter having a bore therein for optically connecting said light guide in said elongated pipe of said endoscope with said light source of said light source unit when said adapter is attached to both said socket of said light source unit and said connector of said endoscope.

2. An endoscope with an adapter according to claim 1, wherein said main body portion of said adapter includes an electrically insulating cylindrical body having two sides, said first and second connecting portions being formed on respective ones of said two sides thereof.

3. An endoscope with an adapter according to claim 2, wherein said cylindrical body has an end face at one side thereof, and a cavity portion in said end face for receiving said connector, said first electrical contact comprising an elastic member elastically projecting into said cavity portion.

4. An endoscope with an adapter according to claim 3, wherein said cylinder body has another end face at the other side thereof, and said second electrical contact includes a contact pin protruding from said another end face of said cylindrical body.

5. An endoscope with an adapter according to claim 4, wherein said adapter includes a fitting means engaging said socket of said light source unit to secure the connection between said second connecting portion and said socket.

6. An endoscope with an adapter according to claim 5, wherein said fitting means includes a fitting ring coaxially mounted on the outer circumference of said cylindrical body and being movable toward said socket for pressing said cylindrical body against said socket when said fitting ring is moved toward said socket.

7. An endoscope with an adapter used in combination with a light source unit including a cylindrical socket having electrical contacts and an external thread formed on the outer circumference thereof, and a light source for illumination, comprising:

an endoscope including a cylindrical connector having opposed end faces; a plurality of exposed electrical contacts; a first elongated pipe projecting from one end face of said connector and having a light guide therein; and a second elongated pipe opening into the interior of said endoscope; and an adapter including a main cylindrical body portion having opposed end faces and being formed of an electrically insulating material, said adapter having: a first connecting portion at one end face of said adapter and adapted to be removably coupled to said connector of said endoscope and a second connecting portion at the other end face of said adapter and adapted to be removably attached to said socket of said light source unit; a plurality of first electrical contacts exposed on one end face of said main cylindrical body for severally electrically connecting with said exposed electrical contacts of said connector; a plurality of second electrical contacts exposed on the other end face of said main cylindrical body, severally electrically connected with said first electrical contacts, and for being severally electrically connecting with said electrical contacts of said socket of said light source unit; first and second bores in said main cylindrical body and extending from said one end face to said other end face for penetrating said first and second elongated pipes respectively; and a fitting ring coaxially fitted on the outer circumference of said main cylindrical body portion and being axially movable on said main cylindrical body portion, said fitting ring having a first engaging portion for engaging said main cylindrical body portion and a second engaging portion for engaging said external thread of said socket of said light source unit.

8. An endoscope with adapter according to claim 7, wherein said second engaging portion of said fitting ring comprises an internal thread formed on the inner circumferential surface of said fitting ring for mating with said external thread of said socket.

9. An endoscope with an adapter according to claim 7, wherein said second engaging portion of said fitting ring includes an engaging lever having a rubbed portion for engaging said external thread of said socket and being urged to rock toward said external thread.

10. An endoscope with adapter according to claim 7, wherein said electrical contacts of said socket are exposed on the outer circumferential surface of said socket.

11. An endoscope with adapter according to claim 7, wherein said socket has an end face, and said electrical contacts of said socket are exposed on said end face of said socket.

* * * * *

UNITED STATES PATENT AND TRADEMARK OFFICE
CERTIFICATE OF CORRECTION

PATENT NO. : 4,414,608

DATED : November 8, 1983

INVENTOR(S) : Hiroyuki FURIHATA

It is certified that error appears in the above-identified patent and that said Letters Patent is hereby corrected as shown below:

Column 6, line 57 (claim 9), change "rubbed" to --rugged--.

Signed and Sealed this

Fifteenth Day of May 1984

[SEAL]

Attest:

Attesting Officer

GERALD J. MOSSINGHOFF

Commissioner of Patents and Trademarks